(12) United States Patent
Rogers et al.

(10) Patent No.: US 10,653,680 B2
(45) Date of Patent: May 19, 2020

(54) TREATMENT OF IMPULSIVITY-RELATED DISORDERS

(71) Applicant: OXFORD UNIVERSITY INNOVATION LIMITED, Botley (GB)

(72) Inventors: Robert David Rogers, Beaumaris (GB); Trevor Sharp, Oxford (GB)

(73) Assignee: OXFORD UNIVERSITY INNOVATION LIMITED, Botley, Oxford (GB)

( * ) Notice: Subject to any disclaimer, the term of this patent is extended or adjusted under 35 U.S.C. 154(b) by 0 days.

(21) Appl. No.: 16/097,239

(22) PCT Filed: Apr. 27, 2017

(86) PCT No.: PCT/GB2017/051174
§ 371 (c)(1),
(2) Date: Oct. 26, 2018

(87) PCT Pub. No.: WO2017/187176
PCT Pub. Date: Nov. 2, 2017

(65) Prior Publication Data
US 2019/0111029 A1    Apr. 18, 2019

(30) Foreign Application Priority Data

Apr. 28, 2016    (GB) .................................. 1607388.4

(51) Int. Cl.
| | | |
|---|---|---|
| A61K 31/41 | (2006.01) |
| A61K 31/428 | (2006.01) |
| A61K 45/06 | (2006.01) |
| A61P 25/34 | (2006.01) |
| A61P 25/36 | (2006.01) |
| A61P 25/32 | (2006.01) |
| A61P 25/16 | (2006.01) |
| A61K 9/00 | (2006.01) |

(52) U.S. Cl.
CPC ............ *A61K 31/428* (2013.01); *A61K 31/41* (2013.01); *A61K 45/06* (2013.01); *A61P 25/16* (2018.01); *A61P 25/32* (2018.01); *A61P 25/34* (2018.01); *A61P 25/36* (2018.01); *A61K 9/0019* (2013.01); *A61K 9/0053* (2013.01)

(58) Field of Classification Search
CPC ........ A61K 31/41; A61K 31/428; A61P 25/30
USPC .................. 548/121, 207, 209; 514/359, 373
See application file for complete search history.

(56) References Cited

U.S. PATENT DOCUMENTS 4,935,429 A * 6/1990 Dackis .................. A61K 31/135
                                                                 514/288
6,001,848 A * 12/1999 Noble .................... A61K 31/48
                                                                 514/282

FOREIGN PATENT DOCUMENTS

| EP | 1884234 A1 | 7/2012 |
| WO | 1999049860 A1 | 10/1999 |
| WO | 2006096759 A2 | 9/2006 |
| WO | 2006123676 A1 | 11/2006 |
| WO | 2012107735 A2 | 8/2012 |
| WO | 2015200358 A1 | 12/2015 |

OTHER PUBLICATIONS

Atack, et al., "Inositol Monophosphatase—a Putative Target for Li+ in the Treatment of Bipolar Disorder", Trends in Neurosciences, 18(8), 1995, 343-349.

(Continued)

*Primary Examiner* — Deepak R Rao
(74) *Attorney, Agent, or Firm* — Liang & Hennessey LLP; Stanley D. Liang (57) ABSTRACT le;2qThe invention relates to the treatment of impulsivity-related disorders, such as a substance-related addiction, a behavioural addiction, relapse to a substance-related or behavioural addiction, a habit or impulsive disorder, an emotional unstable personality disorder, intentional self harm, an eating disorder, a dopamine agonist-induced impulse control disorder, or attention deficit hyperactivity disorder (ADHD) by administering a compound of Formula I or a salt thereof to a subject; Formula (I) wherein: E is S or Se; $R_1$ and $R_2$ are optional substituents, and are at each occurrence independently selected from: (1) a halogen, which is preferably selected from F, Cl and Br; (2) $C_1$-$C_4$ alkyl, such as $C_1$-$C_2$ alkyl or $C_1$ alkyl, optionally substituted with one or more halogen atoms, each of which is preferably selected from F, Cl and Br; and (3) $C_1$-$C_4$ alkoxy, such as $C_1$-$C_2$ alkoxy or $C_1$ alkoxy; optionally substituted with one or more halogen atoms, each of which is preferably selected from F, Cl and Br; m is an integer in the range of from 0 to 5; and n is an integer in the range of from 0 to 4. The compound can also be used to treat or control impulsivity control disorders in patients undergoing dopamine agonist treatment, for example in patients suffering from Parkinson's disease or ADFID.

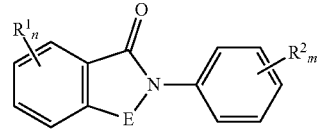

Formula I

14 Claims, 5 Drawing Sheets

(56) References Cited

OTHER PUBLICATIONS

GB Search Report received in GB1607388.4 dated Feb. 15, 2018 (3 pages).
Hollander, et al., "Does Sustained-Release Lithium Reduce Impulsive Gambling and Affective Instability Versus Placebo in Pathological Gamblers With Bipolar Spectrum Disorders", American Journal of Psychiatry., 162(1), Jan. 1, 2005, 137-145, pp. 9.
International Search Report & Written Opinion received in PCT/GB2017/051174 dated Jun. 22, 2017 (13 pages).
Ledesma, et al., "Reduction in Central $H_2O_2$ Levels Prevents Voluntary Ethanol Intake in Mice: A Role for the Brain Catalase-$H_2O_2$ System in Alcohol Binge Drinking", Alcoholism: Clinical and Experimental Research, 38(1), Jan. 1, 2014, 60-67, pp. 2.
Masaki, et al., "Effects of the Potential Lithium-mimetic, Ebselen, on Impulsivity and Emotional Processing", Psychopharmacology, Springer Verlag, Berlin, DE, 233(14), Jun. 2, 2016, 2655-2661, pp. 12.
Singh, et al., "A Safe Lithium Mimetic for Bipolar Disorder", Nature Communications, 4, Jan. 8, 2013, 1332., pp. 7.
Singh, et al., "Effect of the Putative Lithium Mimetic Ebselen on Brain Myo-Inositol, Sleep, and Emotional Processing in Humans", Neuropsychopharmacology, 41(7), Nov. 23, 2015, 1768-1778, pp. 11.
English machine translation of WO 2066123676 (produced with WIPO translate).
Ledesma, et al., "Reduction in Central H2O2 Levels Prevents Voluntary Ethanol Intake in Mice: A Role for the Brain Catalase-H2O2 System in Alcohol Binge Drinking", Alcoholism: Clinical and Experimental Research, 38(1), Jan. 1, 2014, 60-67.

\* cited by examiner

Schematic of the rodent gambling task (from Barrus et al; J. Neuroscience, 2016, 36(3), 785-794)

TREATMENT OF IMPULSIVITY-RELATED DISORDERS

TECHNICAL FIELD

The present invention relates to the treatment of impulsivity and disorders related to impulsivity, in particular to compounds that can be used to treat or control such disorders.

BACKGROUND

A number of psychiatric conditions are linked to impulsive behaviour, including suicidal behaviour, addictive conditions such as drug, alcohol and gambling addiction, eating disorders, aggression, and self-mutilating behaviour. It has been estimated that in Europe, there were 15.5 million cases of addiction that required treatment in 2010, costing a total of €65.7 billion (Olesen et al.; European Journal of Neurology, 2012, 19, 155-162). Therefore, the prevalence and the societal and financial consequences of such disorders are substantial.

Lithium is currently one of the few pharmacological treatments that has some activity in impulsivity-related disorders. Lithium suffers from the problem of toxicity, its toxic level being only twice that of its therapeutic concentration. It requires frequent blood level monitoring which is inconvenient and expensive. It can also cause side effects such as polyurea, polydypsia, and kidney damage, in addition to interfering with thyroid function. It can also cause adverse interactions with other commonly known used drugs, which limits the clinical populations where it can be used.

The physiological basis for impulse control disorders is not clear. Although a link between lithium and inhibition of the enzyme inositol monophosphatase is thought to be responsible for its ability to treat bipolar disorder (Berridge et al., Cell, 1989, 59, 411-419), lithium itself has a diverse range of biochemical effects, which could also explain its high toxicity and side-effect profile (Atack et al., Trends in Neurosciences, 1995, 18(8), 343-349 and Medicinal Research Reviews, 1997, 17(2), 215-224).

Therefore, there is a need for alternative treatments for conditions related to impulsivity that are less toxic than lithium, can be used in a wider clinical population, and which have better compatibility with other commonly used drugs.

SUMMARY OF INVENTION

According to the present invention, there is provided a compound of Formula I, or a pharmaceutically acceptable salt thereof, for use in the treatment or control of impulsivity-related conditions.

Formula I

In Formula I:
E is S or Se;
$R^1$ and $R^2$ are optional substituents, and are at each occurrence independently selected from:

(1) a halogen, which is preferably selected from F, Cl and Br;
(2) $C_1$-$C_4$ alkyl, such as $C_1$-$C_2$ alkyl or $C_1$ alkyl, optionally substituted with one or more halogen atoms, each of which is preferably selected from F, Cl and Br; and
(3) $C_1$-$C_4$ alkoxy, such as $C_1$-$C_2$ alkoxy or $C_1$ alkoxy; optionally substituted with one or more halogen atoms, each of which is preferably selected from F, Cl and Br;
m is an integer in the range of from 0 to 5; and
n is an integer in the range of from 0 to 4.

An example of a compound falling within the scope of Formula I is ebselen (2-phenyl-1,2-benzisoselenazol-3(2H)-one).

The impulsivity-related conditions that can be treated or controlled include those that are characterised by impulsive actions that have the potential to cause harm to the self or others.

These include, but are not limited to, habit and impulse disorders, examples of which are listed in the World Health Organisation's International Statistical Classification of Diseases and Related Health Problems, version 10 (ICD-10) under the category "F63—Habit and Impulse Disorders", and include pyromania, kleptomania, trichotillomania, and intermittent explosive disorder.

Treatable disorders also include behavioural addictive disorders, such as gambling disorder, binge eating disorder, excessive use of computers, the internet or video games, sexual addiction, and addiction to shopping.

The disorders also include substance-related addictions, such as drug or alcohol dependency, for example dependency on psychoactive substances such as alcohol, opioids, cannabinoids, sedatives or hypnotics, cocaine, stimulants such as caffeine, hallucinogens, tobacco, volatile solvents or combinations thereof (e.g. ICD-10 categories F 10.2 to F 19.2).

The compounds can also help avoid relapse to addictive behaviour or substance-related addictions, for example in patients who are undergoing or who have undergone rehabilitation after misuse of or addiction to drugs or alcohol, for example the psychoactive substances listed above.

Other disorders include those characterised by impulsive or emotional and unstable personality disturbance or disorders, for example aggressive, borderline or explosive personality disorder, as encompassed by ICD-10 category F60.3.

Further conditions include those characterised by intentional self-harm or self-mutilation, for example purposely self-inflicted injuries as described in ICD-10 categories X78 and X79—"Intentional self-harm by sharp or blunt object"), and also eating disorders such as binge eating disorder, compulsive eating disorders giving rise to metabolic disorders or to weight gain or obesity disorders, bulimia nervosa and anorexia nervosa.

In addition, the compounds can help control or treat impulsivity control disorders in patients that are undergoing dopamine-targeted drug therapy, as used for example in treating Parkinson's disease or attention deficit hyperactivity disorder (ADHD). In addition, because ADHD does feature impulsivity in its behaviours, the compounds of Formula I or salts thereof can be used to treat ADHD.

The invention also relates to methods of treating or controlling such impulsivity-related disorders, by administering to a subject a therapeutically effective amount of a compound of Formula I or a salt thereof, or a pharmaceutical composition comprising a compound of Formula I or a salt thereof.

The invention further relates to the use of a compound of Formula I or salt thereof in the manufacture of a medicament for the treatment or control of such impulsivity-related disorders.

BRIEF DESCRIPTION OF THE DRAWINGS

The present invention will now be described with reference to the accompanying drawings, in which:

In FIGS. 3 to 5, * indicates a statistically significant effect ($p<0.05$).

DESCRIPTION OF EMBODIMENTS

The compounds of Formula I described herein have previously been shown to be capable of inhibiting the enzyme inositol monophosphatase (IMPase), and to have utility in treating bipolar disorder (WO 2012/107735; Singh et al.; Nature Communications, 2013, DOI: 10.1038/ncomms2320). However, a link between IMPase inhibition and effects on impulsivity and the conditions described above has not previously been established.

It has now been found that compounds of Formula I can reduce certain impulsive behaviours in human and animal models, and hence can be used to treat or control associated conditions.

The Compounds

The compounds of the invention are of Formula I as shown below, or a pharmaceutically acceptable salt thereof.

Formula I

In Formula I, E is S or Se;

$R^1$ and $R^2$ are at each occurrence independently selected from:
(1) a halogen, which is preferably selected from F, Cl and Br;
(2) $C_1$-$C_4$ alkyl, such as $C_1$-$C_2$ alkyl or $C_1$ alkyl, optionally substituted with one or more halogen atoms, each of which is preferably selected from F, Cl and Br; and
(3) $C_1$-$C_4$ alkoxy, such as $C_1$-$C_2$ alkoxy or $C_1$ alkoxy; optionally substituted with one or more halogen atoms, each of which is preferably selected from F, Cl and Br.

m is an integer in the range of from 0 to 5.

n is an integer in the range of from 0 to 4.

The hydrogen atoms of either one or both the phenyl rings in the compound of Formula I can optionally be substituted with one or more substituents $R^1$ or $R^2$, in which each substituent is at each occurrence selected independently from:
(1) a halogen, which is preferably selected from F, Cl and Br, more preferably from F and Cl;
(2) $C_1$-$C_4$ alkyl, such as $C_1$-$C_2$ alkyl or $C_1$ alkyl, optionally substituted with one or more halogen atoms, each of which is preferably selected from F, Cl and Br, more preferably from F and Cl; and
(3) $C_1$-$C_4$ alkoxy, such as $C_1$-$C_2$ alkoxy or $C_1$ alkoxy; optionally substituted with one or more halogen atoms, each of which is preferably selected from F, Cl and Br, more preferably from F and Cl.

There can be up to four $R^1$ substituents and up to five $R^2$ substituents, i.e. n can be up to 4 and m can be up to 5.

In embodiments, n and m are each no more than 2, and preferably are no more than 1. Even more preferably, only one of n and m is greater than zero, and more preferably the non-zero value is 1. Most preferably, both n and m are zero.

The compound has the structure of Formula I, or is a pharmaceutically acceptable salt thereof. In a preferred embodiment, the compound is not a salt.

One example of a compound of Formula I is 2-phenyl-1,2-benzisoselenazol-3(2H)-one, otherwise known as ebselen. Its structure is shown in Formula II.

Formula II

Ebselen is capable of transferring across the blood/brain barrier (WO 2012/107735). Ebselen is also known to be sufficiently non-toxic in humans at pharmaceutically effective dosages, having already been through clinical trials for treating ischemic stroke (Yamaguchi et al; Stroke, 1998, 29, 12-17) and hence is a strong candidate for future clinical trials. The LD50 concentration of ebselen is greater than 1000 mg/kg in rats.

Another example of a compound of Formula I is 2-phenyl-1,2-benzisothiazol-3(2H)-one. Its structure is shown in Formula III below:

Formula III

Ebselen and 2-phenyl-1,2-benzisothiazol-3(2H)-one can be provided in the form of a pharmaceutically acceptable salt. They can each be formulated as outlined below, and in the dosages as described below.

FORMULATIONS

The compounds of Formula I described herein, or pharmaceutically acceptable salts thereof, can be delivered to a patient by intradermal, intramuscular, intraperitoneal, intravenous, subcutaneous, intranasal, or oral routes, for example. They can be administered by any convenient means, for example by infusion or bolus injection, by absorption through epithelial or mucotaneous linings (e.g. oral mucosa, rectal and intestinal mucosa). Administration can be systemic or local.

The compounds of Formula I described herein, or pharmaceutically acceptable salts, thereof, can be formulated as a medicament, which preferably takes the form of therapeutically effective individual doses of the compound of Formula I or salt thereof, adjusted to the form of administration.

For oral administration, the medicament can be formulated into solid or liquid preparations, such as pills, tablets, troches, capsules, powder, granules, syrups, solutions, suspensions or emulsions.

Solid medicaments can comprise one or more of the following in addition to the desired quantity of the compound of Formula I or salt thereof: a pharmaceutically active carrier, including conventional ingredients such as lactose, sucrose and cornstarch; binders such as acacia, cornstarch or gelatine; disintegrating agents, such as potato starch or alginic acid; and lubricants such as stearic acid or magnesium stearate. Optionally, the medicament can be a sustained release formulation, in which the ebselen is incorporated in a matrix of an acrylic polymer or chitin, for example.

Examples of liquid medicaments for oral administration include aqueous solutions such as syrups, flavoured syrups, aqueous or oil suspensions, optionally flavoured emulsions with edible oils, and elixirs. Suspensions can include dispersing or suspending agents such as synthetic and natural gums, for example tragacanth, acacia, alginate, dextran, sodium carboxymethylcellulose, methylcellulose, polyvinylpyrrolidone and gelatin.

For parenterally-administered medicaments, the compound of Formula I or salt thereof is typically formulated with a suitable liquid injection vehicle, which include for example water, saline, dextrose, water-miscible solvents such as ethanol, polyethylene glycol and propylene glycol, and non-aqueous vehicles such as plant or animal oils. Optionally, the medicament can be an emulsion. Optionally, the pH is typically in the range of from 6 to 8, preferably 6.5 to 7.5. Optionally, buffers such as citrates, acetates or phosphates, can be present. Optionally, antioxidants such as ascorbic acid or sodium bisulphite can be present. Optionally, solubilising agents and stabilisers such as cyclodextrin, lysolecithin, oleic acid, stearic acid, and dextrin can be present. Optionally, local anaesthetics such as lignocaine and procaine hydrochloridecan can be present. Formulations such as those described in U.S. 2004/0029934, comprising phosphatidylcholine and phosphatidylethanolamine, and those described in U.S. 2004/0053888 comprising cyclodextrin, can be used.

Doses

The compounds of Formula I, or salt thereof, are suitable for treating a mammalian subject, for example a human.

Suitable doses of the compound of Formula I or salt thereof are in the range of from 5 to 5000 mg for a human patient per day, for example from 50 to 2000 mg per day, from 200 to 1000 mg per day, or from 200 to 600 mg per day.

The compound of Formula I or salt thereof can be provided in one dose, or more than one dose, typically in the range of from two to eight doses per day, for example from two to four or from two to three doses per day. In one embodiment, the compound of Formula I or salt thereof can be administered in the form of an orally administered solution or suspension in water. An example of a dosage regime would be the administration of a solution or suspension comprising 100 mg of the compound of Formula I or salt thereof in water 3 times per day, or 150 mg in water twice daily. In another embodiment, capsules, pills or tablets comprising the compound of Formula I or salt thereof for oral administration can be provided, for example the administration of 1, 2, 3, 4 or 8 capsules, pills or tablets each comprising 200 mg of the compound of Formula I or salt thereof per day.

Typically, for human administration, each individual dose comprises in the range of from 5 to 500 mg of the compound of Formula I, or salt thereof, for example from 50 to 400 mg, or from 100 to 300 mg, such as 200 mg.

Combinations

The compounds or salts described herein can be administered in combination with one or more further compounds.

For example, more than one compound of Formula I or salt thereof can be used.

Alternatively, or additionally, one or more compounds of Formula I (or salt thereof) can be used in combination with dopamine-targeted (dopamine agonist) drug treatments, for example for Parkinson's disease or ADHD, which can cause disabling impulse-control disorders in patients. Dopamine agonists include apomorphine, bromocriptine, cabergoline, ciladopa, dihydrexidine, dinapsoline, doxanthrine, epicriptine, L-DOPA, lisuride, pergolide, piribedil, pramipexole, propylnorapomorphine, quinagolide, ropinirole, rotigotine, roxindole and sumanirole.

Administration of combinations can be simultaneous, sequential or separate, and can be provided in the form of a kit comprising the two or more active ingredients, either combined together in a single medicament, or separately in the form of separate medicaments.

Treatable Conditions

The impulsivity-related conditions that can be treated or controlled include those that are characterised by impulsive actions that have the potential to cause harm to the self or others.

These include, but are not limited to, habit and impulse disorders, examples of which are listed in the World Health Organisation's International Statistical Classification of Diseases and Related Health Problems, version 10 (ICD-10) under the category "F63—Habit and Impulse Disorders", and include pyromania, kleptomania, trichotillomania, and intermittent explosive disorder.

These disorders also include behavioural addictive disorders, such as gambling disorder (problem or pathological gambling), binge eating disorder, excessive use of computers, the internet or video games, sexual addiction, and addiction to shopping.

The disorders also include substance-related addictions, such as drug or alcohol dependency, for example dependency on psychoactive substances such as alcohol, opioids, cannabinoids, sedatives or hypnotics, cocaine, stimulants such as caffeine, hallucinogens, tobacco, volatile solvents or combinations thereof (e.g. ICD-10 categories F 10.2 to F 19.2).

The compounds can also help avoid relapse to addictive behaviour, for example in patients who are undergoing or who have undergone rehabilitation after misuse of or addiction to drugs or alcohol, for example the psychoactive substances listed above, or who are undergoing or who have undergone treatment for a behavioural addiction.

Other disorders include those characterised by impulsive or emotional and unstable personality disturbance or disorders, for example aggressive, borderline or explosive personality disorder, as encompassed by ICD-10 category F60.3.

Further conditions include those characterised by intentional self-harm or self-mutilation, for example purposely self-inflicted injuries as described in ICD-10 categories X78 and X79—"Intentional self-harm by sharp or blunt object"), and also eating disorders such as binge eating disorder or compulsive eating disorders such as those which which give rise to metabolic disorders or to weight gain or obesity disorders. Further eating disorders include bulimia nervosa and anorexia nervosa.

In addition, the compounds can help control or treat impulsivity control disorders in patients that are undergoing by dopamine-targeted drug therapy, as used for example in treating Parkinson's disease or ADHD.

ADHD itself features impulsivity amongst its behaviours. The compounds of Formula I or salts thereof can therefore be used in the treatment of ADHD, or the impulsive symptoms of ADHD.

As mentioned above, these disorders are not suicide-related, i.e. not associated with suicide attempts, or suicidal thoughts or tendencies. For example, intentional self injury is clinically distinct from suicidal behaviour.

Tests that can be used to evaluate impulsivity include experiments on humans, for example the Cambridge Gambling Task (CGT), and also experiments on animals, for example the rodent Gambling Task (rGT) and the 5 Choice Serial Reaction Time Task (5 CSRTT).

EXPERIMENTAL

Experiment 1—Human Studies

Ethical approval for the study was obtained from the National Research Ethics Service Committee (NRES), South-Central Oxford, UK.

Twenty healthy participants (7 females, 13 males; mean age 25.1 years, range 20-38 years; mean BMI 22.7 kg/m$^2$, range 18.7-30.0 kg/m$^2$) were included in the study after giving full informed written consent.

Exclusion criteria included a history of any DSM-5 Axis I psychiatric disorder (determined using the Standard Clinical Interview for Diagnostic and Statistical Manual for Mental Health Disorders), significant current medical condition, current regular medication (apart from the contraceptive pill), pregnancy or lactation, heavy smoking (defined as more than 5 cigarettes per day) and having taken part in another study involving an investigational drug within the previous 3 months. Participants were asked to maintain stable exercise and diet as well as refrain from alcohol during study participation.

Ebselen capsules and identical matching placebo (containing microcrystalline cellulose) were purchased from Shasun Pharmaceuticals Ltd. Participants were tested twice (seven days apart) receiving on one occasion ebselen and, on the other, placebo in a randomised, double-blind, cross-over design. Ebselen was administered in 6×200 mg capsules in three doses given over two days. The order of receiving either the ebselen or the placebo was randomised.

On the day before cognitive testing, participants took the first dose at 1 pm and the second dose at 10 pm. The final dose was taken around 3 hrs prior to cognitive testing. Participants were sent text message reminders a few minutes before they were due to take medication, and were asked to confirm receipt of the messages. The cognitive tasks were carried out immediately after a magnetic resonance spectroscopy study.

On the screening visit, participants were assessed for baseline depression and anxiety symptoms with the Beck Depression Inventory (Beck et al.; Arch. Gen. Psychiatry; 1961, 4: 561-571) and the state measure of the State-Trait Anxiety Inventory (STAI) (Spielberger et al.; Manual for the State-Trait Anxiety Inventory, Consulting Psychologists Press, Palo Alto Calif., 1983), and for personality with the Eysenck Personality Questionnaire (Eysenck and Eysenck, Manual of the Eysenck Personality Questionnaire, London: Hodder & Stoughton, 1975). On the morning preceding psychological testing, the Leeds Sleep Evaluation Questionnaire (LSEQ) was completed within 30 minutes of waking (Parrot and Hindmarch, Psychopharmacology, 1980, 71, 173-179).

Before cognitive testing, participants were asked to rate their mood using the Positive and Negative Affective Schedule (PANAS) (Watson et al.; J. Pers. Soc. Psychol., 1988, 54, 1063-1070), to complete a side effect profile using a 4-point rating scale and also to guess as to whether they had received ebselen or placebo on that randomization arm.

CGT Procedure

The Cambridge Gambling Task (CGT) from the Cambridge Neuropsychological Test Automated Battery (CANTAB, version 3.0.0, Cambridge Cognition Ltd., Cambridge, UK) (Rogers et al.; Neuropsychopharmacology, 1999, 20, 322-333; Clark et al.; Brain, 2008, 131, 1311-1322) assesses decision-making and risk-taking behaviour outside a learning context. In each trial, participants are shown ten boxes at the top of the screen, with some boxes being red and some being blue. The ratio of red to blue boxes varies from 9:1; 8:2; 7:3; 6:4; 5:5 and vice versa in a pseudo-random order.

Participants are informed that a yellow token is hidden inside one of the boxes and asked to indicate the colour box in which the token is most likely to be hidden, by pressing the colour (RED or BLUE) in a response panel at the bottom of the screen. Following their response, the participants indicate confidence in their selection by betting a proportion of points they are allocated (starting with 100 points). Besides confidence in selection, this measure also assesses the willingness to risk the points they already possess or have accumulated for further real or perceived reward. On each trial five bets are offered, and each bet represents a fixed percentage of the current total points score (5, 25, 50, 75 and 95%). Possible bets are presented sequentially in a box on the right of the display and participants touch the box to select the bet. If correct, the bet value is added to their total points on the left of the panel, and if incorrect, it is subtracted from the total points.

Participants are asked to accumulate as many points as possible. Following the response the location of the token is revealed. Participants perform the task in four blocks of two separate conditions, ascending and descending bet value (the condition order is counterbalanced across participants). In the ascending condition, bets increase at 2.5 s time intervals from 5% to 95% until participants make their selection. This means that if a participant bets at the first value presented, then they bet only 5% of their total points, and if they wait for the highest value, they bet 95% of their total points. In the descending condition bets start from 95% and decrease to 5%. Low bets in the ascend condition and high bets in the descend condition reveal an impulsive betting strategy, while high bets in both conditions reveal a risk taking or reward seeking strategy.

From the first stage of the task (selecting the likely colour of the box in which the token is hidden), the outcome measures are deliberation time and quality of decision making. Deliberation time is the mean latency from presentation of coloured boxes to participant selection. Quality of decision making refers to the proportion of trials on which the more likely outcome is chosen. From the gamble stage, the outcome measures are risk taking, risk adjustment and delay aversion. Risk taking refers to the mean proportion of current points that the subject stakes on each gamble when the more likely outcome is selected, and can be regarded as an index of reward seeking or loss aversion.

Risk adjustment measures the degree to which a subject varies their risk taking in response to the ratio of red to blue boxes on each trial. Delay aversion is the difference between the risk-taking score in the descend and the ascend condition.

Analysis

Statistical analyses were performed in SPSS version 22. Analyses were conducted with repeated measures ANOVA with 'treatment' (ebselen vs placebo) and 'order' (placebo first vs ebselen first) as within-subject factors. Significant differences on the ANOVA were followed up with pairwise comparisons using paired samples t-tests.

Results

At baseline, all participants had low scores on self-rating scales of mood and anxiety. There were no main or interactive effects of the ebselen treatment on mood, assessed using subjective mood ratings using the positive and negative affective schedule (PANAS) questionnaire for the placebo and ebselen study visits (Table 1). The number of participants who correctly guessed the randomisation arm at east visit is also shown.

TABLE 1

Subjective PANAS mood ratings

| | Placebo Mean ± SEM | Ebselen Mean ± SEM | Statistical Significance |
|---|---|---|---|
| PANAS - Positive | 28.5 ± 1.6 | 29.8 ± 1.2 | $F_{1, 19} = 1.7, p = 0.204$[a] |
| PANAS - Negative | 11.8 ± 0.7 | 11.9 ± 0.7 | $F_{1, 19} = 0.1, p = 0.818$[a] |
| Correct guesses for randomisation | 14/20 (70%) | 7/20 (35%) | $p = 0.056$ $(\chi^2)$[b] |

[a]Repeat measures ANOVA
[b]Chi-squared statistic

Ebselen was well tolerated and no participants dropped out of the study. Five participants reported feeling drowsy while on ebselen treatment, compared with none reporting this effect while on placebo treatment. Otherwise, there was a low and comparable frequency of side effects reported during ebselen and placebo treatment. There were no significant differences in the subjective measures of sleep assessed using the LSEQ. Participants were more likely to guess correctly that they had received placebo in comparison to ebselen, but the difference was of borderline significance.

Results of the CGT are shown in Table 2.

Figure 1:
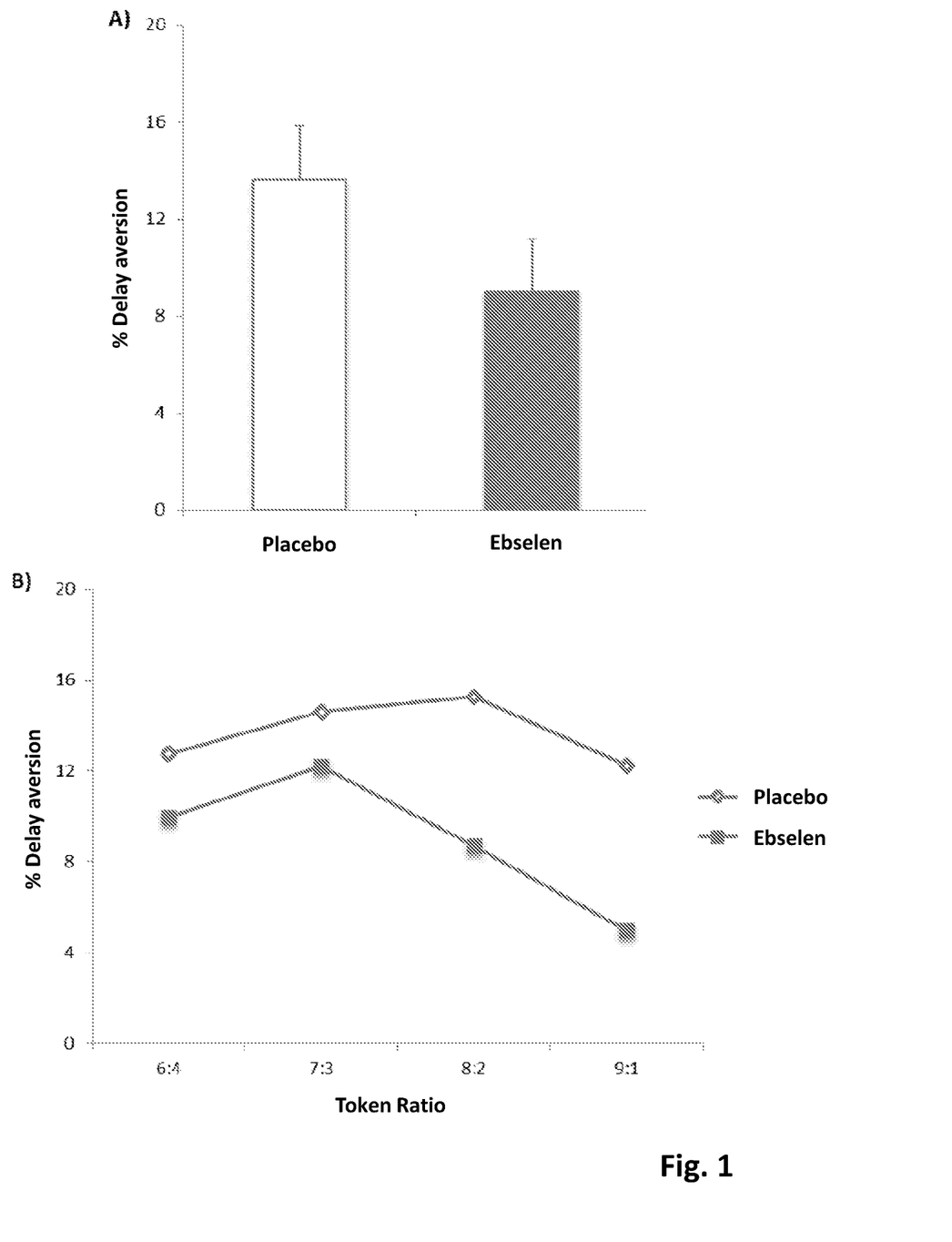
FIGS. 1A and 1B show the effects of ebselen versus control in the Cambridge Gambling Task.

There were no significant effects of treatment on the quality of decision making, deliberation time or risk adjustment. However, ebselen treatment was associated with a significant decrease in delay aversion. This effect was present irrespective of the probability of a favourable outcome and also irrespective of the token ratio presented, as shown in FIGS. 1A and 1B.

TABLE 2

CGT Results

| | Placebo Mean ± SEM | Ebselen Mean ± SEM | Statistical Significance[a] |
|---|---|---|---|
| Delay aversion (%) | 13.7 ± 2.19 | 9.0 ± 2.14 | $F_{1, 18} = 8.21, p = 0.010$ |
| Reward seeking (%) | 60.3 ± 1.82 | 63.9 ± 1.45 | $F_{1, 18} = 4.61, p = 0.046$ |
| Deliberation time (ms) | 1475 ± 99 | 1408 ± 78 | $F_{1, 18} = 2.50, p = 0.131$ |
| Quality of decision making (%) | 98.3 ± 0.8 | 99.3 ± 0.3 | $F_{1, 18} = 0.20. p = 0.155$ |
| Risk adjustment | 2.3 ± 0.15 | 2.1 ± 0.18 | $F_{1, 18} = 2.88, p = 0.107$ |

[a]Repeated measures ANOVA

Ebselen treatment was also associated with an increase in reward seeking/risk taking. There was also a significant interaction between order and treatment on deliberation time ($F_{1,18}$=38.41, p=0.001). There were no other significant main or interactive effects of order on the remaining measures on the CGT.

Discussion of Results

This experiment shows that ebselen diminishes a laboratory measure of impulsivity.

The CGT provides measures of decision making as well as impulsive responding. "Delay aversion" is measured by subtracting the bets made on ascending trials from those of the descending trials. In this task, low bets in the ascend conditions coupled with high bets in the descend condition reveal a more impulsive form of responding, and this difference in bets on the two conditions was diminished by ebselen, suggesting that it can help decrease impulsive behaviour. Therefore, the results indicate that ebselen (and other compounds of Formula I) can be used to treat conditions relating to such impulsive behaviour, particularly those relating to addictive disorders (e.g. addiction to drugs, alcohol or gambling), impulse conduct disorders (e.g. pyromania, kleptomania, trichotillomania and intermittent explosive disorder, behavioural addictive disorders, eating disorders, and intentional self-harm).

Experiment 2—Rodent Models

Testing was carried out in Vancouver (Canada) using rats (males; Long Evans from Charles River) which were given at least two weeks to acclimatise to the animal facility. They were housed in pairs on a 12 hour reverse light-dark cycle (lights off at 7 am). In the second week of acclimatisation, rats were handled briefly each day. Food was then restricted and progressively decreased to 14 g/rat/day over the next week. For each task, there was then a habituation session to the operant boxes before training began.

Measurement of 5-$HT_{2A}$ function was carried out in Oxford (UK) using rats (males, Hooded Lister from Harlan) housed in fours on a 12 hour light-dark cycle (lights on at 7 am). In the second week of acclimatisation, rats were handled briefly each day.

All experiments were approved by local ethical committees and followed national guidelines for animal welfare (Canadian Council of Animal Care, or the UK Animals (Scientific Procedures) Act 1986).

Ebselen, cocaine and 2,5-dimethoxy-4-iodoamphetamine (DOI) were obtained from Sigma Aldrich, and MDL 100, 907 was obtained from Tocris. Ebselen was dissolved in 0.5M DMSO and made up to injection volume (8 ml/kg)

using 4% cyclodextrin. Cocaine and DOI were dissolved in 0.9% saline. MDL 100,907 was dissolved in 0.9% saline and the pH was adjusted to 6.25 using 1M NaOH and 0.1M HCl.

All data for the cognitive tasks are presented as mean+ SEM change from baseline:

performance on drug day–performance on the previous day

The data were analysed with repeated measures ANOVA with dose as a within-subject factor. Where appropriate, post-hoc analysis was performed using Student's paired t-test.

In experiments investigating the effect of ebselen on cocaine and DOI, data were analysed with a two-way ANOVA with ebselen and cocaine/DOI as between-subject factors. If an interaction was detected, this was further investigated using simple main effects analysis. All analyses were conducted using SPSS 22 with p<0.05 considered significant.

5-CSRTT Procedure

This test was performed as described previously (Bari et al., Nature Protocols, 2008, 3(5), 759-767; Robbins, Psychopharmacology, 2002, 163(3), 362-380).

Fourteen rats were trained to respond to brief visual cues presented in one of five target areas with an inter-trial interval of 5 seconds. On the day of testing in the presence of ebselen, the inter-trial interval was lengthened to 7 seconds to cause a reliable increase in premature responding.

Ebselen and vehicle were administered by intraperitoneal (i.p.) injection 1 hour prior to testing. Three doses of ebselen (2, 5 or 10 mg/kg) were studied, administration being in a random order that was determined by a Latin square design. Rats were run five days a week, with the treatment day falling on day three. This ensured the rats did not habituate to the lengthened inter-trial interval, and also provided additional data for both pre- and post-drug administration.

Following ebselen, 3 doses of MDL 100,907 (0.01, 0.03 and 0.1 mg/kg, i.p.) were tested in a Latin square design with the first injection occurring one week after the final injection of ebselen. MDL 100,907 is a selective 5-HT$_{2A}$ antagonist. Rats were similarly run five days a week with injections falling on the third day, and the lengthened inter-trial interval was used only on the drug-administration day.

The Latin square design (for both the 5-CSRTT and rGT experiments) was counterbalanced, based on performance in the last training day of each task. A one week wash-out period was given between drug-administration days. A baseline session was performed both the day before and the day after treatment to ensure stable off-drug performance.

To assess the effect of ebselen on stimulant-induced responding, ebselen (10 mg/kg) or vehicle was administered 1 hour prior to cocaine (15 mg/kg i.p.), which in turn was administered 10 minutes prior to testing. Treatments were administered using according to a Latin square design. The inter-trial interval for these sessions was 5 seconds. Two rats were excluded from the data due to increasing levels of omissions across all days of this portion of the study. The experiment was repeated using 0.03 mg/kg MDL 100,907 instead of ebselen.

rGT Procedure

Figure 2:
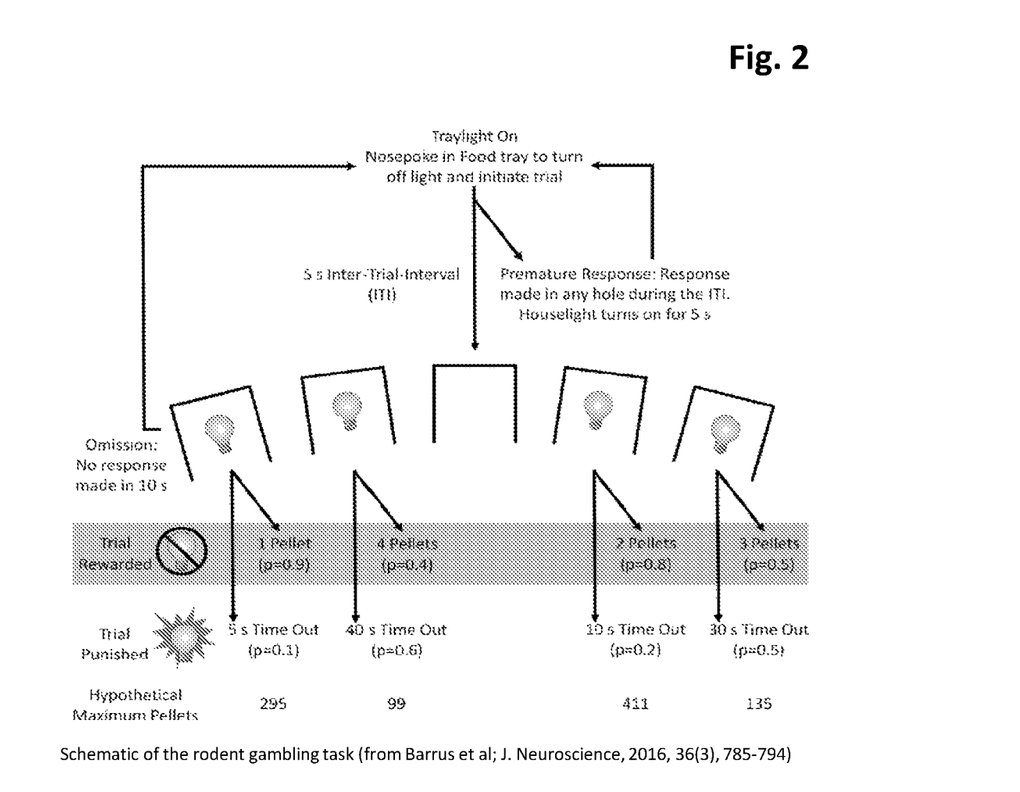
FIG. 2 is a schematic illustration of the Rodent Gambling Test.

This was performed as described previously (Zeeb et al; Neuropsychopharmacology, 2009, 34(10), 2329-2343), and is illustrated schematically in FIG. 2. Twenty one rats were trained to respond in standard 5-CSRTT boxes. Once reliable responding was established, different reward contingencies were associated with four nose-poke apertures (the central aperture was not used in this task). In each case, the reward size and probability of outcome differed between the choices. When no reward was delivered, a fixed-length time-out was delivered. The length of this time-out was varied between choices, with the longest time-out being associated with the largest, least likely reward. The optimal choice was the "P2" choice which resulted in a reward of 2×45 mg sucrose pellets 80% of the time when this choice was made. On the other 20% of occasions, a 10 second time-out was initiated. Once stable performance was achieved, rats were administered ebselen (2, 5 and 10 mg/kg i.p.) or vehicle in a Latin square design.

Results

Figure 3:
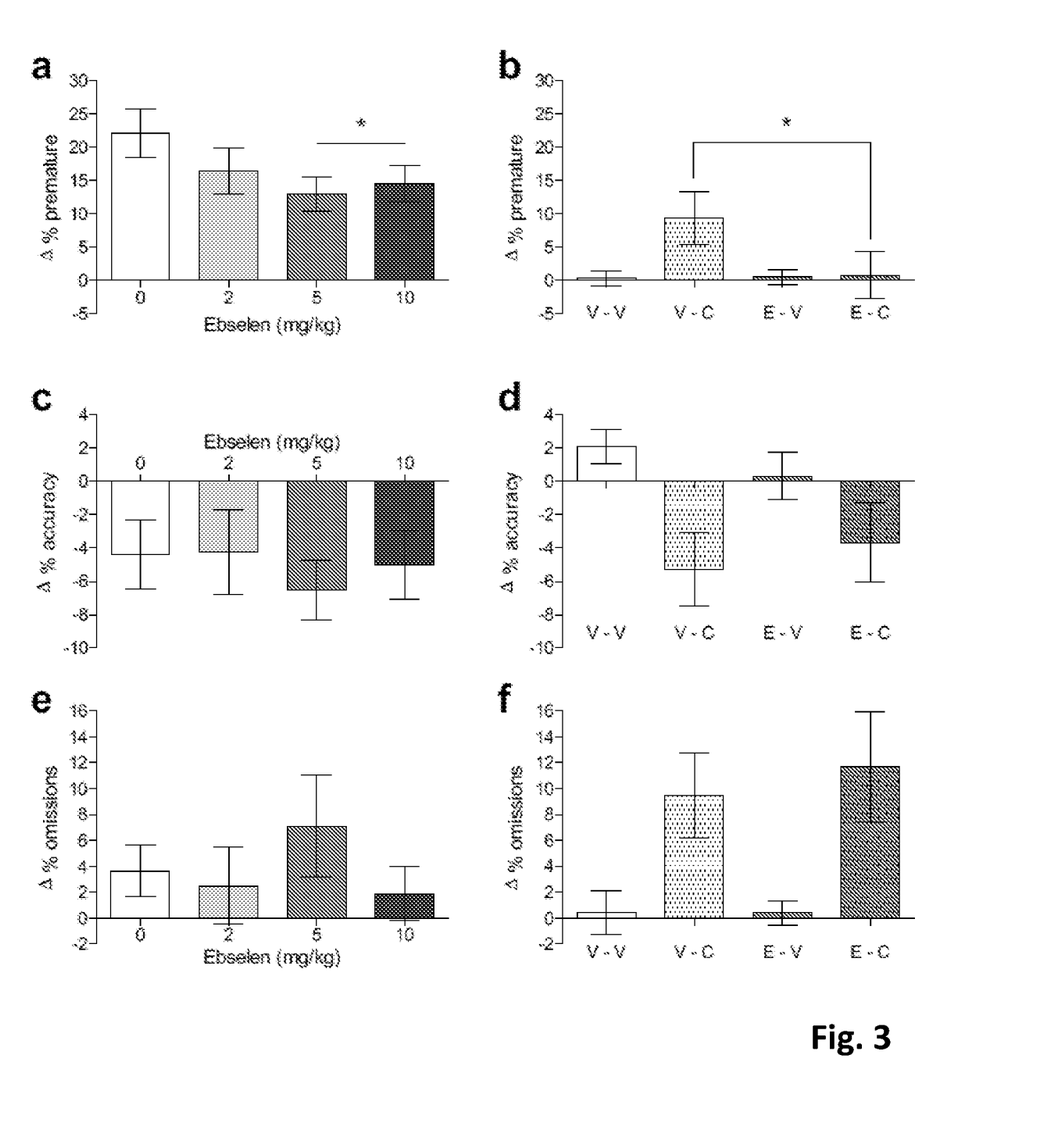
FIGS. 3a, 3c and 3e show the effects of ebselen versus control on rats in the 5 Choice Serial Reaction Time Task.
FIGS. 3b, 3d and 3f show the effects of ebselen versus control on rats in the 5 Choice Serial Reaction Time Task after administration of cocaine.

In the 5 CSRTT, ebselen decreased premature responding in a dose-dependent manner compared to vehicle controls ($F_{3,39}$=2.870, p=0.049). No effect of ebselen was detected at 2 mg/kg when compared to vehicle treatment (t(13)=1.498, p=0.158) but both 5 mg/kg (t(13)=2.977, p=0.011) and 10 mg/kg (t(13)=2.402, p=0.032) led to statistically significant decreases in premature responding. No effects of ebselen were detected on any other measures ($F_{3,39}$=1.656–0.329, p=0.192–0.805). These results are illustrated in FIGS. 3a, c and e.

Figure 4:
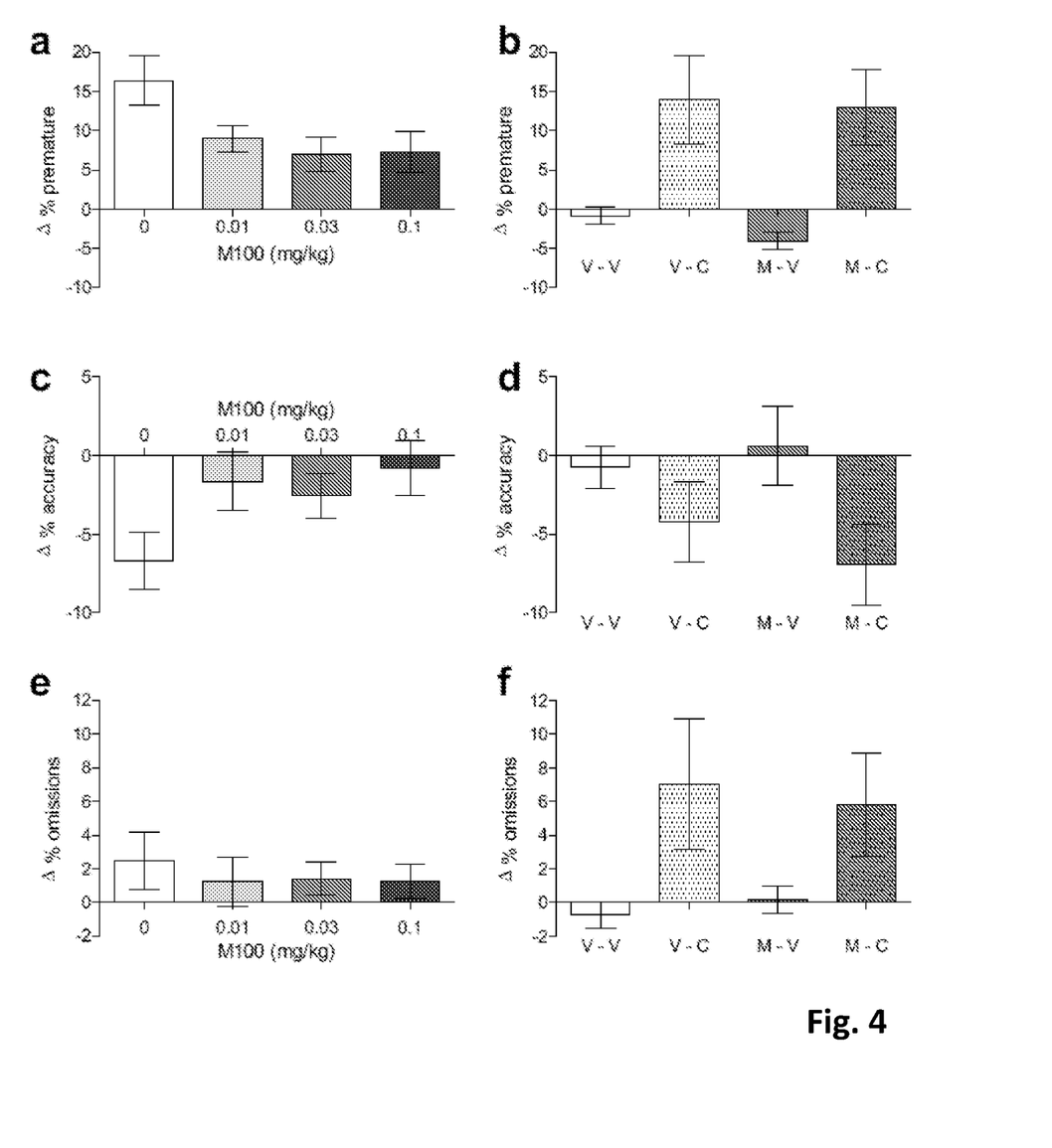
FIGS. 4a, 4c and 4e show the effects of MDL 100,907 versus control on rats in the 5 Choice Serial Reaction Time Task.
FIGS. 4b, 4d and 4f show the effects of MDL 100,907 versus control on rats in the 5 Choice Serial Reaction Time Task after administration of cocaine.

MDL 100,907 also decreased premature responding at all dosage levels (0.01, 0.03 and 0.1 mg/kg i.p.) compared to vehicle controls ($F_{3,39}$=5.870, p=0.002; Paired t-tests: 0 versus 0.01 mg/kg, t(13)=3.117, p=0.008; 0 versus 0.03 mg/kg, t(13)=3.096, p=0.009; 0 versus 0.1 mg/kg, t(13)=4.536, p=0.001). MDL 100,907 also significantly negated the decrease in accuracy that was seen following vehicle injection ($F_{3,39}$=3.078, p=0.039), both at 0.01 mg/kg (t(13)=2.645, p=0.020) and at 0.01 mg/kg (t(13)=2.496, p=0.027), with a trend at 0.03 mg/kg (t(13)=2.142, p=0.052). MDL 100,907 had no detectable effects on other parameters ($F_{3,39}$=0.234–1.766, p=0.170–0.872). Results are illustrated in FIGS. 4 a, c and e.

Ebselen (10 mg/kg i.p.) reduced cocaine-induced premature responses in the 5 CSRTT. The overall ANOVA revealed a strong effect of ebselen on premature response ($F_{1,11}$=5.442, p=0.040) that interacted with the effects of cocaine ($F_{1,11}$=5.998, p=0.032). No overall effect of cocaine was seen ($F_{1,11}$=1.635, p=0.227). Post-hoc paired t-tests revealed a reduction in premature responding when ebselen was injected before cocaine (t(11)=2.628, p=0.023). Moreover, the number of premature responses made following ebselen/cocaine treatment did not differ from that following vehicle/vehicle treatment (t(11)=−0.117, p=0.909). Statistically, the increase in premature responses seen following cocaine administration when rats did not receive ebselen was only a trend (t(11)=2.080, p=0.062).

Cocaine alone had significant effects on both accuracy ($F_{1,11}$=15.189, p=0.002) and omission rates ($F_{1,11}$=6.702, p=0.025). These effects were not reversed by ebselen (Accuracy: ebselen, $F_{1,11}$=0.002, p=0.969; ebselen×cocaine interaction, $F_{1,11}$=1.302, p=0.278; Omissions: ebselen, $F_{1,11}$=0.579, p=0.463; ebselen×cocaine interaction, $F_{1,11}$=0.579, p=0.4653). No effects were seen on any other measure ($F_{1,11}$=2.782–0.061, p=0.124–0.810).

The effects of ebselen and cocaine are shown in FIGS. 3b, d and f. In these Figures, V-V=vehicle/vehicle; V-C=vehicle/cocaine; E-V=ebselen/vehicle; and E-C=ebselen/cocaine.

In contrast to ebselen, MDL 100,907 did not reduce cocaine-induced increases in premature responding. Cocaine increased premature responding ($F_{1,11}$=10.627, p=0.008) but this was not affected by MDL 100,907 (MDL 100,907: $F_{1,11}$=1.277, p=0.282; M 100,907×cocaine interaction: $F_{1,11}$=0.196, p=0.667). Results are shown in FIGS.

4b, d and f In these Figures, V-V=vehicle/vehicle; V-C=vehicle/cocaine; M-V=M100,907/vehicle; and M-C=M100,907/cocaine.

Correct response latency was decreased by cocaine ($F_{1,11}$=7.537, p=0.019) while MDL 100,907 resulted in an increased trend ($F_{1,11}$=3.968, p=0.072), but these two effects did not interact statistically ($F_{1,11}$=0.047, p=0.832). There was also a trend for cocaine increase omissions ($F_{1,11}$=4.292, p=0.063), but no other effects were seen ($F_{1,11}$=3.195-0.009, p=0.101–0.925).

Figure 5:
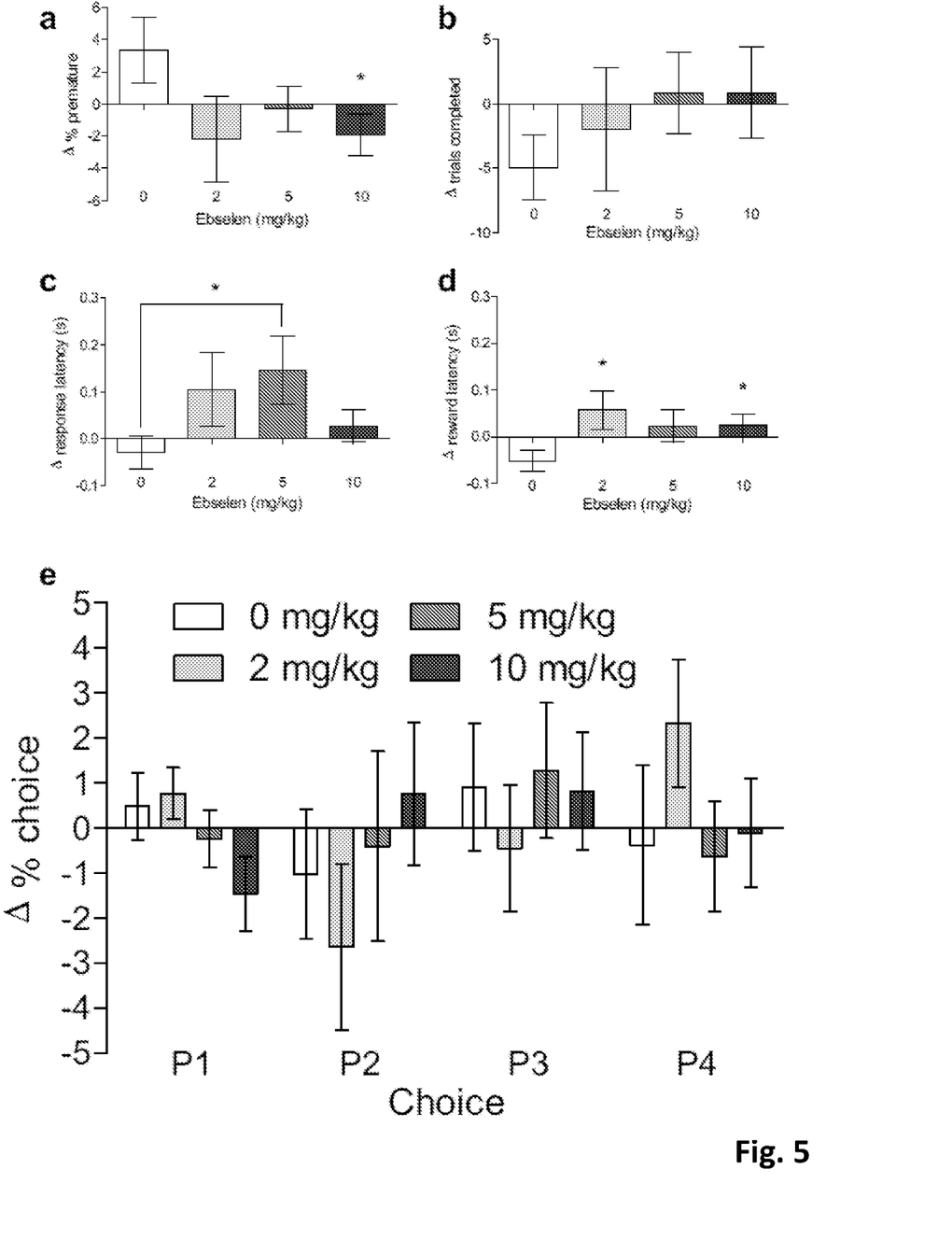
FIGS. 5a to 5e shows the effects of ebselen versus control in the Rat Gambling Test.

In the rGT, ebselen (2, 5 and 10 mg/kg i.p.) showed an overall trend to decreased premature responses ($F_{3,60}$=2.286, p=0.088). However, if paired t-tests were run comparing each dose of ebselen against the vehicle control group, clear effects were revealed, although the effect was not dose-related. Whereas ebselen at 2 and 10 mg/kg doses decreased premature responses (t(20)=2.063, p=0.052 and t(20)=2.366, p=0.028 respectively), the 5 mg/kg dose had a decreased trend (t(20)=1.866, p=0.077). These results are illustrated in FIG. 5a.

Ebselen had no effect on choice behaviour (effect of choice: $F_{3,60}$=0.635, p=0.596; dose×choice interaction $F_{9,180}$=0.712, p=0.698). Ebselen also had no effect on the number of trials completed during the sessions ($F_{3,60}$=0.716, p=0.546), response latency ($F_{3,60}$=2.262, p=0.090) or reward latency ($F_{3,60}$=2.575, p=0.062). In the case of response latency, paired t-tests revealed a trend for 2 mg/kg ebselen to increase the time to respond (t(20)=2.029, p=0.056), and this effect was significant at the 5 mg/kg dose (t(20)=2.369, p=0.028). 10 mg/kg showed no significant effect (t(20)=1.194, p=0.246). Reward latency showed a trend increase following 5 mg/kg ebselen (t(20)=1.866, p=0.069), with both other doses leading to a significant increase in the time taken to collect rewards (2 mg/kg: t(20)=2.063, p=0.024; 10 mg/kg: t(20)=2.366, p=0.005). These results are shown in FIGS. 5b to 5e.

In summary, ebselen reduces premature responding in the 5-CSRTT and rGT. However, a 5-$HT_{2A}$ receptor antagonist MDL 100,907 did not produce the same effects across all tests, in particular tests involving the effects of cocaine. This indicates that ebselen, and other compounds of Formula I, do not necessarily impact the 5-$HT_{2A}$ receptor, and instead act via different or additional mechanisms.

With regard to the cocaine-related tests, because cocaine tends to increase brain dopamine concentrations, then inhibition of the effects of cocaine on impulsivity indicates that impulsivity-related conditions induced by dopamine agonist treatments can be controlled by ebselen, and other compounds of Formula I or their salts.

Consequently, the compounds or salts of Formula I, such as ebselen, can be used in a combined treatment with dopamine agonists to reduce or control impulsivity-related conditions or side effects.

The invention claimed is:

1. A method of treating a condition selected from a substance-related addiction, a behavioural addiction, relapse to a substance-related or behavioural addiction, a habit or impulsive disorder, an emotional unstable personality disorder, intentional self-harm, an eating disorder, a dopamine agonist-induced impulse control disorder, or Attention Deficit Hyperactivity Disorder (ADHD), comprising administering a therapeutically effective amount of a compound of Formula I or a pharmaceutically acceptable salt thereof to a human subject in need thereof, wherein Formula I is;

Formula I wherein:
E is S or Se;
$R^1$ and $R^2$ are optional substituents, and are at each occurrence independently selected from:
(1) a halogen;
(2) $C_1$-$C_4$ alkyl, optionally substituted with one or more halogen atoms; and
(3) $C_1$-$C_4$ alkoxy; optionally substituted with one or more halogen atoms;
m is an integer in the range of from 0 to 5; and
n is an integer in the range of from 0 to 4.

2. The method of claim 1, wherein n and m in Formula I are each no more than 2.

3. The method of claim 1, wherein the sum of n and m in Formula I is no more than 1.

4. The method of claim 1, wherein the compound of Formula I is 2-phenyl-1,2-benzisoselenazol-3(2H)-one (ebselen) or 2-phenyl-1,2-benzisothiazol-3(2H)-one.

5. The method of claim 1, wherein at least one of the following applies to the condition treated:
the substance-related addiction is addiction to one or more psychoactive substances;
the habit or impulsive disorder is selected from pyromania, kleptomania, trichotillomania and intermittent explosive disorder;
the behavioural addiction is selected from gambling disorder, binge eating disorder, excessive use of computers, the internet or video games, addition to shopping and addiction to sex;
the emotionally unstable personality disturbance or disorder is selected from borderline personality disorder, aggressive personality disorder and explosive personality disorder;
the eating disorder is selected from bulimia nervosa, anorexia nervosa, binge eating disorder, and compulsive eating disorders;
the dopamine-agonist induced impulsive control disorder is associated with dopamine agonist treatment of Parkinson's disease or ADHD; or
the treatment or control of ADHD is for treatment or control of the impulsive symptoms associated with ADHD.

6. The method of claim 1, wherein the condition is substance-related addiction to one or more psychoactive substances, and the psychoactive substance is selected from alcohol, opioids, cannabinoids, sedatives or hypnotics, cocaine, hallucinogens, tobacco, volatile solvents, stimulants, or combinations of any one or more thereof.

7. The method of claim 1, wherein the condition is a substance-related addiction, a behavioural addiction, relapse to a substance-related or behavioural addiction, or a habit or impulsive disorder.

8. The method of claim 1, wherein the condition is not associated with suicide attempts, or suicidal thoughts or tendencies.

9. The method of claim 1, wherein the subject is a human.

10. The method of claim 9, wherein the treatment comprises administering one or more doses per day of the compound or salt of Formula I to the human subject.

11. The method of claim 10, wherein the total daily dose of the compound or salt of Formula I administered is in the range of from 5 to 2000 mg per day.

12. The method of claim 1, wherein the compound or salt of Formula I is administered with one or more dopamine agonists.

13. The method of claim 12, wherein the one or more dopamine agonists are selected from apomorphine, bromocriptine, cabergoline, ciladopa, dihydrexidine, dinapsoline, doxanthrine, epicriptine, L-DOPA, lisuride, pergolide, piribedil, pramipexole, propylnorapomorphine, quinagolide, ropinirole, rotigotine, roxindole and sumanirole.

14. The method of claim 10, wherein the total daily dose of the compound or salt of Formula I administered to the human subject is in the range of from 200 to 1000 mg per day.

* * * * *